United States Patent [19]

Kudoh et al.

[11] Patent Number: 4,937,353

[45] Date of Patent: Jun. 26, 1990

[54] PREPARATION PROCESS FOR INDOLES

[75] Inventors: Akihide Kudoh, Yokohama; Tadatoshi Honda, Hiratsuka; Makoto Kotani; Kazuhiro Terada, both of Yokohama; Takeshi Tsuda, Kouza; Shinji Kiyono, Yokohama, all of Japan

[73] Assignee: Mitsui Toatsu Chemicals, Incorporated, Tokyo, Japan

[21] Appl. No.: 267,708

[22] Filed: Nov. 3, 1988

Related U.S. Application Data

[63] Continuation of Ser. No. 903,609, Sep. 5, 1985, abandoned, which is a continuation of Ser. No. 736,577, May 21, 1985, abandoned, which is a continuation of Ser. No. 506,002, Jun. 17, 1983, abandoned.

[30] Foreign Application Priority Data

Jun. 24, 1982 [JP] Japan ................. 57-107537

[51] Int. Cl.$^5$ ................. C07B 37/10; C07D 209/08
[52] U.S. Cl. ................. 548/508
[58] Field of Search ................. 548/508

[56] References Cited

U.S. PATENT DOCUMENTS

| | | | |
|---|---|---|---|
| 4,376,205 | 3/1983 | Matsuda et al. | 548/508 |
| 4,436,916 | 3/1984 | Matsuda et al. | 548/508 |
| 4,436,917 | 3/1984 | Matsuda et al. | 548/508 |
| 4,443,615 | 4/1984 | Matsuoka et al. | 548/508 |
| 4,456,760 | 6/1984 | Matsuda et al. | 548/508 |
| 4,473,698 | 9/1984 | Matsuda et al. | 548/508 |
| 4,474,969 | 10/1984 | Honda et al. | 548/508 |

FOREIGN PATENT DOCUMENTS

| | | |
|---|---|---|
| 0069242 | 1/1983 | European Pat. Off. |
| 0075019 | 3/1983 | European Pat. Off. |
| 56-150062 | of 1981 | Japan |
| 56-36451 | 4/1981 | Japan |
| 56-46865 | 4/1981 | Japan |
| 56-53652 | 5/1981 | Japan |
| 56-55366 | 6/1981 | Japan |
| 56-86154 | 7/1981 | Japan |
| 56-110672 | 9/1981 | Japan |
| 58-29762 | of 1982 | Japan |
| 57-206656 | of 1982 | Japan |
| 58-35171 | of 1983 | Japan |
| 6100761 | of 1983 | Japan |

OTHER PUBLICATIONS

Abstract of WO82-00032.
Abstract of EP69,242.
Abstract of EP75019.
Abstract of EP86239.
Mitsui, V, Chemical Abstracts, vol. 95, (1981), 150442w, (C.A.).
Hackh's Chemical Dictionary, 3rd Edition (1961), p. 82.
Carl Noller, Textbook of Organic Chemistry, 3rd Edition, (1966), pp. 419-442.
The Merck Index, 9th Edition (1976), No. 2734.
MTC-I, Chem. Abs. 95, 115293b.
MTC-II, Chem. Abs. 95, 115295d.
MTC-III, Chem. Abs. 95, 115294c.
MTC-IV, Chem. Abst. 95, 115296e.

Primary Examiner—Mark L. Berch
Attorney, Agent, or Firm—Fisher, Christen & Sabol

[57] ABSTRACT

Disclosed herein is to react an aniline and an ethylene glycol at a superatmospheric pressure in preparing an indole by subjecting the aniline and ethylene glycol to a gas-phase catalytic reaction in the presence of a catalyst, thereby improving the selectivity of the reaction and the service life of the catalyst.

6 Claims, 1 Drawing Sheet

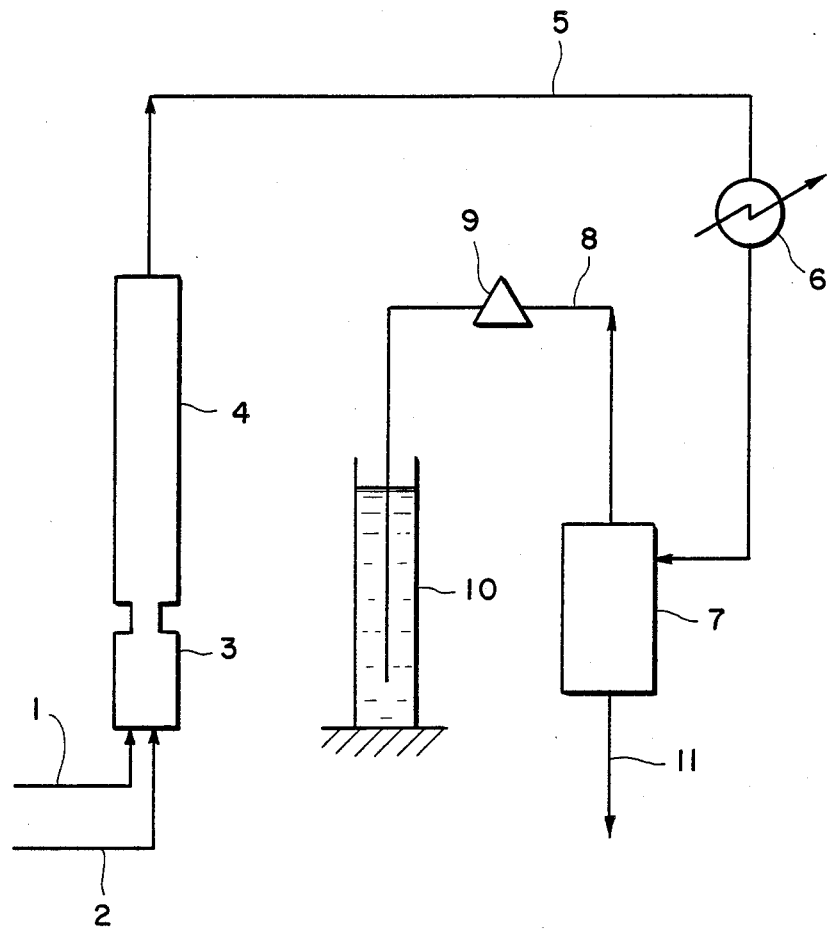

PREPARATION PROCESS FOR INDOLES

This application is a continuation, of application Ser. No. 903,609, filed Sept. 5, 1985, now abandoned which is a continuation of Ser. No. 736,577, filed May 21, 1985 (now abandoned, which is a continuation of Ser. No. 506,002, filed Jun. 17, 1983.

BACKGROUND OF THE INVENTION (1) Field of the Invention

This invention relates to a process for preparing an indole by subjecting an aniline and an ethylene glycol to a gas-phase catalytic reaction at a superatmospheric pressure (2) Description of the Prior Art Indoles have been known as raw materials for the chemical industry and the importance of indole in particular has increased in recent years as raw materials for the syntheses of fragrant substances and amino acids.

A number of attempts have heretofore been made with a view toward synthetically obtaining indoles. However, these attempts were all accompanied by one or more of such problems as many by-products being produced, expensive raw materials being required and multiple step preparation processes being necessary.

Recently, there have been found catalysts effective for reactions in which indoles can be synthesized using anilines and ethylene glycols, inexpensive raw materials, through single step processes (see, for example, Japanese Patent Laid-open Nos. 46865/1981, 110672/1981 and 150062/1981). However, use of such catalysts have been accompanied by such problems as undergoing severe activity reduction due to deposition of hydrocarbons and the like on their surfaces and frequent regeneration and activation treatments being necessary in order to have the catalysts regain their activity.

SUMMARY OF THE INVENTION

An object of this invention is to provide a process for preparing an indole through a gas-phase reaction between an aniline and an ethylene glycol while suppressing the activity reduction of the catalyst and assuring an improved selectivity for the indole.

To achieve the above object, the present inventors engaged in detailed study of the above reaction. As a result, it has been found that the activity reduction of the catalyst may be suppressed to a significant extent by adding water to the reaction system in advance and recycling the reaction gas back to the reaction system. Further study resulted in the surprising finding, contrary to Le Chatelier-Braun's principle, that it is possible not only to suppress the activity reduction of the catalyst but also to improve the selectivity for the formation of the intended indole by carrying out the reaction at a superatmospheric pressure.

In the present invention, for example, aniline reacts with ethylene glycol according to the following formula:

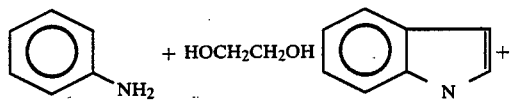
-continued
$H_2 + 2H_2O$

This invention therefore provides a process for preparing an indole by subjecting an aniline and an ethylene glycol to a gas-phase catalytic reaction in the presence of a catalyst, which process comprises carrying out the reaction at a superatmospheric pressure.

BRIEF DESCRIPTION OF THE DRAWING

In the drawing, the single figure is a simplified flow diagram showing the outline of the arrangement of reaction facilities used in Example 1.

DETAILED DESCRIPTION OF THE INVENTION

Anilines useful in the practice of the process according to this invention may be represented by the following general formula (I):

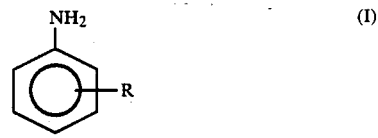

wherein R is a hydrogen or halogen atom or a hydroxyl, alkyl or alkoxyl group. Exemplary anilines may include aniline, o-, m- or p-toluidine, o-, m-, or p-haloaniline, o-, m- or p-hydroxyaniline, or o-, m- or p-anisidine. As illustrative ethylene glycols may be mentioned ethylene glycol, propylene glycol, 1,2-butanediol, 1,2,4- butanetriol, glycerol, 2,3-butanediol, or diethylene glycol.

As catalysts useful in the practice of the process according to this invention, may be mentioned those used in the preparation of indoles through the gas-phase catalytic reactions between anilines and ethylene glycols. The following are examples of such catalysts:

(1) Catalysts containing an oxide or hydroxide of at least one element selected from the group consisting of Si, Al, B, Sb, Bi, Sn, Pb, Ga, Ti, In, Sr, Ca, Zr, Be, Mg, Y, Cu, Ag, Zn, Cd and the lanthanides (hereinafter called "catalyst materials (1)"), including, for example, CdO, ZnO, PbO$_2$, Al$_2$O$_3$—B$_2$O$_3$, SiO$_2$—CaO, SiO$_2$—In$_2$O$_5$, SiO$_2$—SrO, SiO$_2$—CdO, SiO$_2$—Al$_2$O$_3$, SiO$_2$—MgO, TiO$_2$—SnO$_2$, TiO$_2$, —rO$_2$, CdO—Bi$_2$O$_3$, SiO$_2$—Y$_2$O$_3$, SiO$_2$, Bi$_2$O$_3$—BeO, SiO$_2$—Ga$_2$O$_3$, SiO$_2$, —La$_2$O$_3$, SiO$_2$, —Ce$_2$O$_3$, SiO$_2$—ZnO—AgO, or or SiO$_2$—MgO—CuO;

(2) Catalysts containing a sulfide or selenide of at least one element selected from the group consisting of Pd, Pt, Cr, Fe, Ni, Co, Zn, Mo, Cd and W (hereinafter called "catalyst materials (2)"), including, for example, PdS, PtS, CrS, FeS, NiS, CoS, ZnS, MoS2, CdS, WS2, ZnSe, or CdSe;

(3) Catalysts containing an inorganic salt, namely, a halide, carbonate, sulfate, phosphate, pyrophosphate, phosphomolybdate or silicotungstate of an element selected from the group consisting of Fe, Tl, Ca, Mn, Bi, Sr, Y, Al, Zn, Cd, Ni, Mg, In, Be, Co, Ga and the lanthanides (hereinafter called "catalyst materials (3)"), including, for example, ferric sulfate, thallium sulfate, calcium sulfate, manganese sulfate, bismuth sulfate, strontium sulfate, yttrium sulfate, cadmium bromide, aluminum sulfate, zinc sulfate, nickel sulfate, cadmium chloride, magnesium sulfate, indium sulfate, beryllium sulfate, cobalt sulfate, zinc aluminum sulfate, magnesium chloride, cadmium sulfate, or cadmium phosphate, and (4) Metallic catalysts containing at least one element selected from the group consisting of Cu, Ag, Pt, Pd, Ni, Co, Fe, Ir, Os, Ru or Rh (hereinafter called "catalyst materials (4)").

These catalysts may be prepared in any manner known in the art. Namely, the catalyst materials (1) may be prepared by hydrolyzing water-soluble salts of catalyst-constituting elements into their hydroxides and then drying and calcining the thus-obtained gels or by subjecting readily-decomposable salts of catalyst-constituting elements to thermal decomposition in air.

The catalyst materials (2) may be prepared by adding sodium sulfide or potassium selenide to water-soluble salts of catalyst-constituting elements or bringing catalyst-constituting elements or their salts to hydrogen sulfide gas or hydrogen selenide gas.

The catalyst materials (4) may be prepared by reducing salts, hydroxides or oxides of catalyst-constituting elements with a reducing agent such as hydrogen, formaldehyde, formic acid, phosphorous acid, hydrazine or the like.

These catalysts may contain the above-described catalyst materials (1), (2), (3) and (4) either singly or in combination as mixtures. Such catalyst materials may also be carried on carriers. Any conventionally-used carriers may be used but it is common to use diatomaceous earth, pumice, titania, silica-alumina, alumina, magnesia, silica gel, activated carbon, activated clay, asbestos or the like. Carrier-supported catalysts are prepared by causing these carriers to support the above-described catalyst materials in a manner commonly known in the art.

There is no particular limitation to the amount of each of the above catalyst materials to be supported on a carrier. Each of the above catalyst materials may normally be carried in a suitable amount, for example, 1–50% depending on the type of a carrier to be used.

In the preparation process of an indole according to this invention, the reaction between an aniline and an ethylene glycol is carried out in a gas phase and in the presence of one or more of the above catalyst materials. The reaction may be effected in any of a fixed bed reactor, fluidized bed reactor or moving bed reactor.

The aniline and ethylene glycol may be charged into the reactor at a ratio of 1 mole to 0.01–5 moles or, preferably, 0.05–1 mole.

The aniline and ethylene glycol, which are raw materials, may be charged at a total feed rate in the range of 0.01–10 hr$^{-1}$ in terms of liquid hourly space velocity. They may be charged into the reactor after vaporizing in an evaporator in advance. Here, it is feasible to feed, together with the thus-vaporized aniline and ethylene glycol, steam, hydrogen, carbon monoxide, carbon dioxide, methane, nitrogen, neon or argon as a carrier gas. Among these carrier gases, use of steam, hydrogen or carbon monoxide is preferred since they are effective in prolonging the service life of the catalyst.

The reaction temperature may range from 200° to 600° C. or, preferably, from 250° to 500° C.

The term "a superatmospheric pressure" as used herein means a pressure which is above the standard atmospheric pressure and does not permit any components contained in the raw materials to form a condensate phase. Practically speaking, the superatmospheric pressure may preferably range from $1.1 \times 10^5$ Pa to $1.0 \times 10^7$ Pa and, more preferably, from $2.0 \times 10^5$ Pa to $5.0 \times 10^6$ Pa. When a carrier gas is fed together with the raw materials, the total reaction pressure is the sum of the partial pressures of the raw materials and the partial pressure of the carrier gas. Generally speaking, the reaction may be carried out at a higher reaction pressure and a higher LHSV when the reaction temperature is high and at a lower reaction pressure and a lower LHSV when the reaction temperature is low. It is preferable to limit the partial pressure of hydrogen below $1.0 \times 10^6$ when using a catalyst containing a material having high hydrogen-activating capacity and using hydrogen as a carrier gas.

The process according to this invention makes it possible to suppress the reduction of reaction activity and to improve the selectivity of the formation of the intended indole. Although causes for the above advantageous features of the present process have not yet been fully elucidated, they seem to have come about due to certain differences in adsorption characteristics of reaction products onto the catalyst.

The invention will be described in the following Examples:

Examples 1 and Comparative Example 1

An experiment was carried out using the autoclave illustrated in the figure. Packed in a cylindrical reactor 4 made of stainless steel and having an internal diameter of 20 mm were 400 cc of a pellet-like catalyst each 3 mm in diameter and 2.5 mm in height. The catalyst had been formed by tabletting commercial cadimium sulfide. Aniline, ethylene glycol and water were charged through a line 1 at molar ratio of 12:1:8 and at a feed velocity of 600 g/hr into an evaporator 3 while maintaining the temperature of each of the evaporator 3 and a reactor 4 at 350° C. At the same time, hydrogen gas was also charged at 60 lSTP/hr through a line 2 (STP: Standard Temperature and Pressure). The effluent stream was guided from the reactor 4 through a line 5 and into a condenser 6, where it was cooled. The resultant liquid condensate was separated from the gas phase in a gas-liquid separator 7 and discharged through a line 11. The gas phase was delivered through a line 8, depressurized while passing through a reducing valve 9, and discharged through a water-sealed cylinder 10.

The synthesis reaction of the indole was conducted by changing the total reaction pressure as shown in Table 1. Results are also shown in Table 1.

TABLE 1

| | Reaction Pressure (Pa) | Reaction results | Reaction time (hr) 100 | 200 | 300 |
|---|---|---|---|---|---|
| Ex. 1 | $2.0 \times 10^5$ | Conversion of ethylene glycol (%) | 100 | 98 | 91 |
| | | Selectivity of indole based on ethylene glycol (%) | 54 | 56 | 57 |
| | $5.0 \times 10^5$ | Conversion of ethylene glycol (%) | 100 | 100 | 99 |
| | | Selectivity of indole based on ethylene glycol (%) | 75 | 74 | 75 |
| Comp. Ex. 1 | $1.0 \times 10^5$ | Conversion of ethylene glycol (%) | 98 | 86 | 66 |
| | | Selectivity of indole based on ethylene glycol (%) | 44 | 44 | 46 |

Examples 2-5 & Comparative Examples 2-5:

Following the procedure of Example 1, the reaction was carried out by changing the catalyst only. Results are summarized in Table 2.

TABLE 2

|  | Reaction Pressure (Pa) | Catalyst | Reaction results | Reaction time (hr) 100 | 200 | 300 |
|---|---|---|---|---|---|---|
| Ex. 2 | $5.0 \times 10^5$ | Cu—Cr Catalyst ("C-43", product of Catalysts & Chemicals Inc., Far East) | Conversion of ethylene glycol (%) Selectivity of indole based on ethylene glycol (%) | 100 57 | 100 56 | 100 55 |
| Ex. 3 | $5.0 \times 10^5$ | Pt/SiO$_2$ Catalyst (7% Pt carried) | Conversion of ethylene glycol (%) Selectivity of indole based on ethylene glycol (%) | 100 50 | 100 48 | 97 51 |
| Ex. 4 | $5.0 \times 10^5$ | Ag/SiO$_2$ Catalyst (product of Catalysts & Chemicals Inc., Far East; 13% Ag carried) | Conversion of ethylene glycol (%) Selectivity of indole based on ethylene glycol (%) | 100 73 | 100 76 | 99 72 |
| Ex. 5 | $7.0 \times 10^5$ | Cu/SiO$_2$ Catalyst (2.5% Cu carried) | Conversion of ethylene glycol (%) Selectivity of indole based on ethylene glycol (%) | 100 59 | 99 60 | 97 60 |
| Comp. Ex. 2 | $1.0 \times 10^5$ | The same catalyst as used in Ex. 2 | Conversion of ethylene glycol (%) Selectivity of indole based on ethylene glycol (%) | 100 34 | 92 35 | 80 36 |
| Comp. Ex. 3 | $1.0 \times 10^5$ | The same catalyst as used in Ex. 3 | Conversion of ethylene glycol (%) Selectivity of indole based on ethylene glycol (%) | 99 31 | 78 28 | 59 26 |
| Comp. Ex. 4 | $1.0 \times 10^5$ | The same catalyst as used in Ex. 4 | Conversion of ethylene glycol (%) Selectivity of indole based on ethylene glycol (%) | 100 58 | 86 59 | 71 60 |
| Comp. Ex. 5 | $1.0 \times 10^5$ | The same catalyst as used in Ex. 5 | Conversion of ethylene glycol (%) Selectivity of indole based on ethylene glycol (%) | 100 45 | 75 44 | 49 41 |

Example 6

A reaction was carried out following the procedure of Example 1 except that one of the raw materials, aniline, was changed to p-toluidine. Results are shown in Table 3.

Example 7

The procedure of Example 1 was repeated except for the substitution of one of the raw materials, ethylene glycol, with diethylene glycol. Results are also given in Table 3.

Example 8

Following the procedure of Example 1, a reaction was carried out using 1,2-butanediol instead of one of the raw materials, ethylene glycol. Results are summarized in Table 3.

Example 9

Following the procedure of Example 1, a reaction was carried out using m-chloroaniline instead of one of the raw materials, aniline. Results are shown in Table 3.

Example 10

Following the procedure of Example 1, a reaction was carried out using p-anisidine instead of one of the raw materials aniline. Results are shown in Table 3.

TABLE 3

|  | Reaction raw material | | Reaction product | Reaction pressure ($10^5$ Pa) | Selectivity of indole based on ethylene glycol upon an elapsed time of 100 hrs. after initiation of reaction (%) |
|---|---|---|---|---|---|
|  | Aniline | Ethylene glycol | | | |
| Ex. 6 | p-Toluidine | Ethylene glycol | 5-Methylindole | 4.5 | 61 (*26)* |
| Ex. 7 | Aniline | Diethylene glycol | Indole | 9.0 | 45 (17)* |
| Ex. 8 | Aniline | 1,2-Butanediol | 2- and 3-Ethyl-indole | 12.5 | 30 (9)* |
| Ex. 9 | m-Chloro-aniline | Ethylene glycol | 4- and 6-Chloro-indole | 8.0 | 22 (3)* |
| Ex. 10 | p-Anisidine | Ethylene glycol | 5-Methoxy-indole | 4.0 | 20 (4)* |

*Figures in parenthesis indicate selectivity (%) when the reaction were conducted at normal pressure.

Examples 11-20

Using a variety of catalysts independently, a feed consisting of aniline, ethylene glycol and water at a molar ratio of 15:1:30 was charged at a rate of 380 g/hr together with 30 l STP/hr of hydrogen into the reactor. The reaction temperature was 375° C. and the synthesis reaction of each indole was effected at various total reaction pressures. Results are given in Table 4.

TABLE 4

| | Catalyst (Composition: wt. %) | Reaction Pressure ($10^5$ Pa) | Selectivity of indole based on ethylene glycol upon an elapsed time of 100 hrs. after initiation of reaction (%) |
|---|---|---|---|
| Ex. 11 | CuO—SiO$_2$—ZnO—MnO (40-20-30-10) | 16 | 62 (25)* |
| Ex. 12 | CuO—SiO$_2$—ZnO—MgO (30-50-5-15) | 24 | 71 (34)* |
| Ex. 13 | Ag$_2$O—SiO$_2$—ZnO (30-50-20) | 12 | 59 (27)* |
| Ex. 14 | Pd/SiO$_2$ (6% Pd carried) | 20 | 54 (25)* |
| Ex. 15 | Pd/SiO$_2$ (13% Pd carried) | 16 | 69 (31)* |
| Ex. 16 | Ag—Pd/SiO$_2$ (5% Ag and 5% Pd carried) | 24 | 81 (39)* |
| Ex. 17 | Cu/SiO$_2$—CaO (12% Cu carried/95-5) | 24 | 69 (20)* |
| Ex. 18 | Ag/SiO$_2$—CaO (8% Ag carried/95-5) | 24 | 76 (29)* |
| Ex. 19 | CdSO$_4$ | 8 | 58 (14)* |
| Ex. 20 | MgCl$_2$ | 12 | 58 (10)* |

*Figures in parenthesis indicate selectivity (%) when the reactions were conducted at normal pressure.

What is claimed is:

1. In a process for preparing indole by completely vaporizing aniline and ethylene glycol with water and hydrogen to form a gaseous mixture containing the same materials, contacting the gaseous mixture with a catalyst containing one member selected from the group consisting of cadmium sulfide, cadmium sulfate, magnesium chloride and copper-chromium, or a catalyst containing silicon dioxide and a member selected from the group consisting of platinum, silver, copper and palladium, to form a gaseous reaction mixture containing indole, and cooling the reaction mixture to separate therefrom a liquid condensate containing the indole, the improvement wherein the reaction pressure is in the range of from $2.0 \times 10^5$ Pa to $5.0 \times 10^6$ Pa, the partial pressure of hydrogen in the gaseous mixture is below $1.0 \times 10^6$ Pa, the aniline and ethylene glycol are charged in a ratio, respectively, of 1 mole to 0.05 to 1 mole, the total feed of the aniline and ethylene glycol is in the range of 0.01 to 10 hr$^{-1}$ in terms of liquid hourly space velocity, and the reaction temperature is in the range of 250° to 500° C.

2. The process as claimed in claim 1 wherein the catalyst is at least one member selected from the group consisting of platinum, silver, copper and palladium, on a carrier.

3. In a process for preparing indole by completely vaporizing aniline and ethylene glycol with water and hydrogen to form a gaseous mixture containing the same materials contacting the gaseous mixture with a catalyst selected from the group consisting of platinum which is on silicon dioxide, silver which is on silicon dioxide, copper which is on silicon dioxide, cadmium sulfide and copper-chromium, to form a gaseous reaction mixture containing the indole, and cooling the reaction mixture to separate therefrom a liquid condensate containing the indole, the improvement wherein the reaction pressure is in the range of from $2.0 \times 10^5$ Pa $5.0 \times 10^6$ Pa, the partial pressure of hydrogen in the gaseous mixture is below $1.0 \times 10^6$ the aniline and ethylene glycol are charged in a ratio, respectively, of 1 mole to 0.05 to 1 mole, the total feed rate of the aniline and ethylene glycol is in the range of from 0.01 to 10 hr$-1$ in terms of liquid hourly space velocity, and the reaction temperature is in the range of from 250° to 500° C.

4. The process as claimed in claim 3 wherein the catalyst is copper on a silicon dioxide.

5. In a process for preparing indole by completely vaporizing aniline and ethylene glycol with water and hydrogen to form a gaseous mixture containing the same materials, contacting the gaseous mixture with a catalyst selected from the group consisting of palladium carried on silicon dioxide, silver-palladium carried on silicon dioxide, copper carried on SiO$_2$—CaO and silver carried on SiO$_2$—CAO; CuO—SiO$_2$—CaO; CuO—SiO$_2$—ZnO—MNO, CuO—SiO$_2$—ZNO—MgO and Ag$_2$O—SiO$_2$—ZnO; and cadmium sulfate and magnesium chloride, to form a gaseous reaction mixture containing the indole, and cooling the reaction mixture to separate therefrom a liquid condensate containing the indole, the improvement wherein the reaction pressure is in the range of from $2.0 \times 10^5$ Pa to $5.0 \times 10^6$ Pa, the partial pressure of hydrogen in the gaseous mixture is below $1.0 \times 10^6$ Pa, the aniline and ethylene glycol are charged in a ratio, respectively, to 1 mole to 0.05 to 1 mole, the total feed rate of the aniline and ethylene glycol is in the range of from 0.01 to 10 hr$^1$ in terms of liquid hourly space velocity, and the reaction temperature is in the range of from 250° to 500° C.

6. In a process for preparing indole by completely vaporizing aniline and ethylene glycol with water and hydrogen to form a gaseous mixture containing the same materials, contacting the gaseous mixture with a catalyst selected from the group consisting of platinum which is on silicon dioxide, silver which is on silicon dioxide, copper which is on silicon dioxide, cadmium sulfide, copper-chromium, palladium which is on silicon dioxide, silver-palladium which is on silicon dioxide, copper which is on SiO$_2$—CaO, silver which is on SiO$_2$—CaO, CuO—SiO$_2$ZnO—MnO, CuO—SiO$_2$—ZnO—MgO and Ag$_2$O—SiO$_2$—ZnO, cadmium sulfate and magnesium chloride, to form a gaseous reaction mixture containing the indole, and cooling the reaction mixture to separate therefrom a liquid condensate containing the indole, the improvement herein the reaction pressure is in the range of from $2.0 \times 10^5$ Pa to $5.0 \times 10^6$ Pa, the partial pressure of hydrogen in the gaseous mixture is below $1.0 \times 10^6$ Pa, the anilime and ethylene glycol are charged in a ratio, respectively, of 1 mole to 0.05 to 1 mole, the total feed rate of the aniline and ethylene glycol is in the range of from 0.01 to 10 hr$^{-1}$ in terms of liquid hourly space velocity, and the reaction temperature is in the range of from 250° to 500° C.

* * * * *

UNITED STATES PATENT AND TRADEMARK OFFICE
CERTIFICATE OF CORRECTION

PATENT NO. : 4,937,353

DATED : June 26, 1990

INVENTOR(S) : Kudoh et al.

It is certified that error appears in the above-identified patent and that said Letters Patent is hereby corrected as shown below:

Title page:

[63] Continuation of Ser. No. 903,609, Sept. 5, 1986,

Signed and Sealed this

Twenty-first Day of January, 1992

Attest:

HARRY F. MANBECK, JR.

*Attesting Officer*  *Commissioner of Patents and Trademarks*